(12) United States Patent
Park et al.

(10) Patent No.: US 12,322,105 B2
(45) Date of Patent: Jun. 3, 2025

(54) METHOD FOR ANALYZING HUMAN TISSUE ON BASIS OF MEDICAL IMAGE AND DEVICE THEREOF

(71) Applicant: MEDICALIP CO., LTD., Gangwon-do (KR)

(72) Inventors: Sang Joon Park, Seoul (KR); Hyuk Hee Lee, Seoul (KR); Soon Ho Yoon, Seoul (KR)

(73) Assignee: MEDICALIP CO., LTD., Gangwon-do (KR)

( * ) Notice: Subject to any disclaimer, the term of this patent is extended or adjusted under 35 U.S.C. 154(b) by 361 days.

(21) Appl. No.: 17/793,638

(22) PCT Filed: Apr. 5, 2021

(86) PCT No.: PCT/KR2021/004175
§ 371 (c)(1),
(2) Date: Jul. 18, 2022

(87) PCT Pub. No.: WO2022/010075
PCT Pub. Date: Jan. 13, 2022

(65) Prior Publication Data
US 2023/0048734 A1 Feb. 16, 2023

(30) Foreign Application Priority Data
Jul. 6, 2020 (KR) .................. 10-2020-0083047

(51) Int. Cl.
*A61B 6/03* (2006.01)
*A61B 6/00* (2024.01)
(Continued)

(52) U.S. Cl.
CPC .............. *G06T 7/0014* (2013.01); *G06T 7/11* (2017.01); *G06T 7/149* (2017.01); *G06T 7/174* (2017.01);
(Continued)

(58) Field of Classification Search
None
See application file for complete search history.

(56) References Cited

U.S. PATENT DOCUMENTS 11,386,592 B2 * 7/2022 Paysan .................. G06T 7/0012
11,534,136 B2 * 12/2022 Funka-Lea ........... A61B 8/5261
(Continued)

FOREIGN PATENT DOCUMENTS

CN 112825619 A * 5/2021 ............... G06N 3/04
CN 113473896 A * 10/2021 ........... A61B 5/0013
(Continued)

OTHER PUBLICATIONS

"Office Action of Korea Counterpart Application", issued on Dec. 14, 2021, with English translation thereof, pp. 1-9.
(Continued)

*Primary Examiner* — Mohammed Rachedine
(74) *Attorney, Agent, or Firm* — JCIPRNET

(57) ABSTRACT

Disclosed are a method and device for analyzing human tissue on the basis of a medical image. A tissue analysis device generates training data including a two-dimensional medical image and volume information of tissue by using a three-dimensional medical image, and trains, by using the training data, an artificial intelligence model that obtains a three-dimensional size, volume, or weight of tissue by dividing at least one or more normal or diseased tissues from a two-dimensional medical image in which a plurality of tissues are displayed overlapping on the same plane. In addition, the tissue analysis device obtains a three-dimensional size, volume, or weight of normal or diseased tissue from an X-ray medical image by using the artificial intelligence model.

6 Claims, 8 Drawing Sheets

(51) Int. Cl.
*A61B 6/12* (2006.01)
*G06T 7/00* (2017.01)
*G06T 7/11* (2017.01)
*G06T 7/149* (2017.01)
*G06T 7/174* (2017.01)
*G06T 7/62* (2017.01)
*G16H 30/40* (2018.01)
*G16H 50/20* (2018.01)
*G16H 50/50* (2018.01)

(52) U.S. Cl.
CPC ...... *G06T 7/62* (2017.01); *G06T 2207/10116* (2013.01); *G06T 2207/20081* (2013.01); *G06T 2207/30004* (2013.01)

(56) References Cited

U.S. PATENT DOCUMENTS

| | | | |
|---|---|---|---|
| 12,033,247 B2* | 7/2024 | Balashova | G06N 20/00 |
| 2017/0372475 A1 | 12/2017 | Gulsun et al. | |
| 2022/0028129 A1* | 1/2022 | Balashova | G06N 20/00 |

FOREIGN PATENT DOCUMENTS

| | | | |
|---|---|---|---|
| EP | 3828818 A1 * | 6/2021 | ............ G06N 3/045 |
| JP | 2007229023 | 9/2007 | |
| KR | 1020120086084 | 8/2012 | |
| KR | 101482247 | 1/2015 | |
| KR | 101514003 | 4/2015 | |
| KR | 1020180098984 | 9/2018 | |
| KR | 101981202 | 5/2019 | |
| KR | 102044237 | 11/2019 | |
| KR | 1020190125592 | 11/2019 | |
| WO | 2020114632 | 6/2020 | |

OTHER PUBLICATIONS

"Notice of Allowance of Korea Counterpart Application", issued on Apr. 5, 2022, with English translation thereof, pp. 1-4.
Elena Balashova et al., "3D Organ Shape Reconstruction from Topogram Images", Information Processing in Medical Imaging, Lecture Notes in Computer Science, May 22, 2019, pp. 347-359.
"Search Report of Europe Counterpart Application", issued on Feb. 16, 2024, p. 1-p. 8.

* cited by examiner

METHOD FOR ANALYZING HUMAN TISSUE ON BASIS OF MEDICAL IMAGE AND DEVICE THEREOF

TECHNICAL FIELD

One or more embodiments of the present disclosure relate to a method and apparatus for analyzing human tissue on the basis of a medical image, and more particularly, to a method and device for analyzing the size, volume, or weight of particular tissue from a medical image or generating a segmentation image for tissue.

BACKGROUND ART

X-ray imaging, computed tomography (CT), or magnetic resonance imaging (MRI) are methods of capturing an image of the inside of a human body. X-ray imaging transmits X-rays to all human tissues within an X-ray imaging area, and generates a two-dimensional black-and-white image that appears bright or dark depending on an amount of X-ray particles reduced according to the composition of tissue through which the X-rays pass. X-ray imaging is low-cost and easy for imaging, but is limited to accurately identify organs or lesions because several tissues are displayed overlapping each other on one plane. To obtain more accurate tissue images, CT or MRI is required. However, CT or MRI is expensive, and thus, it is an economic burden to the patient.

DESCRIPTION OF EMBODIMENTS

Technical Problem

One or more embodiments of the present disclosure provide a method and device for analyzing various tissues of a human body from an X-ray medical image by using an artificial intelligence model.

Solution to Problem

A tissue analysis method according to an embodiment of the present disclosure includes generating training data including a two-dimensional medical image and information about a three-dimensional size, volume, or weight of tissue by using a three-dimensional medical image; training, by using the training data, an artificial intelligence model that obtains a three-dimensional size, volume, or weight of tissue by dividing at least one or more normal or diseased tissues from a two-dimensional medical image in which a plurality of tissues are displayed overlapping on a same plane; and obtaining a three-dimensional size, volume, or weight of normal or diseased tissue by inputting an X-ray medical image to the artificial intelligence model.

A tissue analysis device according to an embodiment of the present disclosure includes a training data generating unit configured to generate training data including a two-dimensional medical image and information about a three-dimensional size, volume, or weight of tissue by using a three-dimensional medical image; a training unit configured to, by using the training data, train an artificial intelligence model that obtains a three-dimensional size, volume, or weight of tissue by dividing at least one or more normal or diseased tissues from a two-dimensional medical image in which a plurality of tissues are displayed overlapping on a same plane; and a volume calculating unit configured to obtain a three-dimensional size, volume, or weight of normal or diseased tissue by inputting an X-ray medical image to the artificial intelligence model.

Advantageous Effects of Disclosure

According to one or more embodiments of the present disclosure, a three-dimensional size, volume, or weight of tissue may be obtained from a two-dimensional X-ray medical image. In addition, an artificial intelligence model for two-dimensional X-ray medical images is trained by using precisely-labeled two-dimensional X-ray medical images, which are obtained by converting a labeled image from a three-dimensional medical image into a two-dimensional image, as training data, and thus, the accuracy of the artificial intelligence model may be improved. According to another embodiment, an image in which at least one or more tissues are segmented may be generated from an X-ray medical image.

MODE OF DISCLOSURE

Hereinafter, a method and device for analyzing human tissue according to an embodiment of the present disclosure are described in detail with reference to the accompanying drawings.

Figure 1:
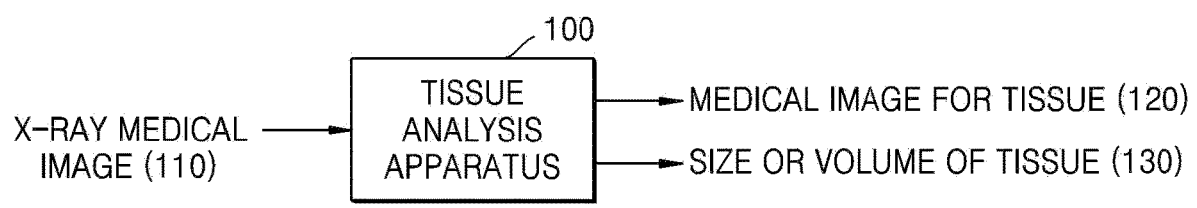
FIG. 1 is a schematic diagram illustrating an example of a tissue analysis apparatus based on a medical image, according to an embodiment of the present disclosure.

FIG. 1 is a schematic diagram illustrating an example of a tissue analysis device based on a medical image, according to an embodiment of the present disclosure.

Referring to FIG. 1, a tissue analysis device 100 receives an X-ray medical image 110 to output a medical image 120 including at least one or more tissues (or a medical image excluding at least one or more tissues) or an analysis result of a three-dimensional size, volume, or weight 130 of at least one or more tissues. Herein, the term 'tissue' refers to any part that may be medically segmented, such as various organs, such as the lungs, bronchial tubes, muscles, fat, the heart, blood vessels, and bones, lesions, such as tumors or the like, or inflammatory areas.

The tissue analysis device 100 is configured to output the medical image 120 for at least one or more tissues from the X-ray medical image 110, is configured to analyze and output the three-dimensional size, volume, or weight 130 of at least one or more tissues from the X-ray medical image 110, or is configured to output both of the medical image 120 and the three-dimensional size, volume, or weight 130.

The tissue analysis device 100 may be implemented as a portion of various medical equipment, such as X-ray imaging equipment or a medical system (e.g., a picture archiving and communication system PACS), or may be implemented as a general computer or server. For example, the tissue analysis device 100 may be used by being implemented as software to be embedded in various medical equipment or medical systems or to be stored in a portable storage medium (e.g., a universal serial bus (USB) memory) and then being connected to an interface of various medical equipment or medical systems.

Figure 2:
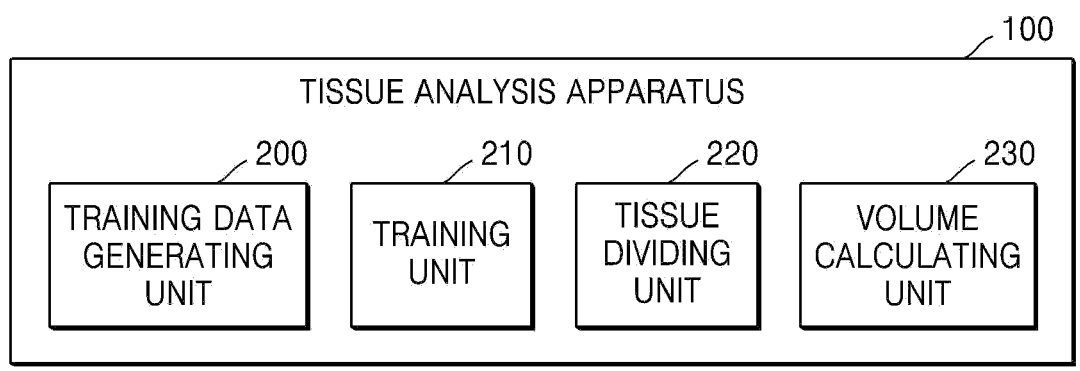
FIG. 2 is a diagram illustrating a configuration of an example of a tissue analysis device according to an embodiment of the present disclosure.

FIG. 2 is a diagram illustrating a configuration of an example of the tissue analysis device according to an embodiment of the present disclosure.

Referring to FIG. 2, the tissue analysis device 100 includes a training data generating unit 200, a training unit 210, a tissue dividing unit 220, and a volume calculating unit 230. According to an embodiment, the tissue analysis device 100 may only include any one of the tissue dividing unit 220 and the volume calculating unit 230. However, for convenience of description, a case in which both of the tissue dividing unit 220 and the volume calculating unit 230 are included is described below. According to another embodiment, the tissue analysis device 100 may include an artificial intelligence model that has been trained, instead of the training unit 210.

The training data generating unit 200 generates training data necessary for training an artificial intelligence model. The artificial intelligence model may be a model that generates a medical image for at least one or more tissues (or a medical image in which at least one or more tissues have been removed) from a two-dimensional X-ray medical image, and/or a model that calculates the three-dimensional size, volume, or weight or the like of at least one or more tissues from a two-dimensional X-ray medical image. Accordingly, to train the artificial intelligence model of the present embodiment, training data, such as a segmentation image (or information about a boundary and brightness value of tissue) or the three-dimensional size, volume, or weight of tissue, is required.

A user with anatomical knowledge may generate training data by dividing particular tissue areas one by one from an X-ray medical image. However, a lot of pieces of training data are needed to train an artificial intelligence model, which is practically impossible for the user to create the pieces training data one by one. In addition, because an X-ray medical image is expressed by overlapping various tissues, the accuracy of tissue division is lowered when each tissue area is divided by simply using brightness or the like, and it is also impossible to generate training data about the three-dimensional size, volume, or weight of tissue from the X-ray medical image.

Accordingly, the present embodiment proposes a method of automatically generating training data from a three-dimensional medical image. A method by which the training data generating unit 200 generates training data necessary for training an artificial intelligence model by using a three-dimensional medical image is described in detail with reference to FIGS. 3 to 5.

Figure 6:
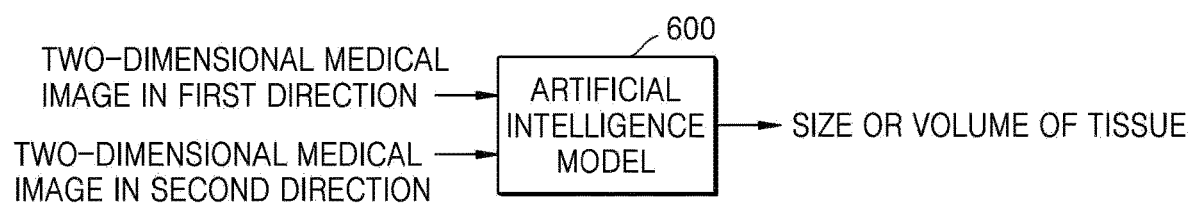
FIG. 6 is a diagram illustrating an example of an artificial intelligence model that obtains the size, volume, or weight of three-dimensional tissue from a two-dimensional X-ray medical image, according to an embodiment of the present disclosure.
Figure 7:
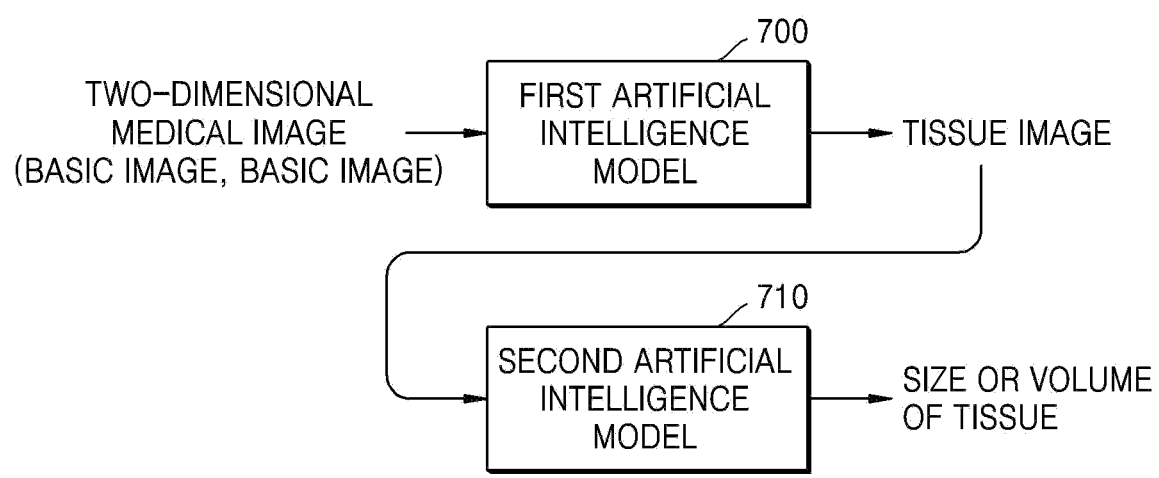
FIG. 7 is a diagram illustrating another example of an artificial intelligence model according to an embodiment of the present disclosure.

The training unit 210 trains an artificial intelligence model by using training data generated by the training data generating unit 200. The artificial intelligence model may be implemented as various architectures, such as a convolutional neural network (CNN), DenseNet, U-net, GoogLeNet, generative adversarial network, or the like. For example, when the artificial intelligence model is implemented as a CNN, the artificial intelligence model performs a training operation of adjusting a connection weight of an artificial neural network by using training data. According to an embodiment, the tissue analysis device 100 may include one or a plurality of artificial intelligence models. For example, the tissue analysis device 100 may include each of an artificial intelligence model that generates a medical image for at least one or more tissues from a two-dimensional X-ray medical image and an artificial intelligence model that calculates the three-dimensional size, volume, or weight of at least one or more tissues from a two-dimensional X-ray medical image, or may include an artificial intelligence model in which the two artificial intelligence models described above are integrated as one. Various implementation embodiments of an artificial intelligence model are shown in FIGS. 6 and 7.

When the tissue dividing unit 220 receives a two-dimensional X-ray medical image, the tissue dividing unit 220 generates and outputs a tissue image including at least one or more normal or diseased tissues by using an artificial intelligence model trained by the training unit 210. A tissue image may include information on a boundary (or area) and brightness of corresponding tissue of an X-ray medical image. In a two-dimensional tissue image, a brightness value reflects the density of corresponding tissue. For example, when the tissue dividing unit 220 receives an X-ray medical image for the chest, the tissue dividing unit 220 may generate and output a tissue image including only lung tissue by using an artificial intelligence model.

As another embodiment, the tissue dividing unit 220 may segment a plurality of tissues included in an X-ray medical image, and may generate and output respective tissue images for the plurality of tissues. For example, when the tissue dividing unit 220 receives an X-ray medical image for the chest, the tissue dividing unit 220 may generate and output respective tissue images for a plurality of different tissues, such as a first tissue image for lung tissue, and a second tissue image for a lesion, such as a tumor.

As another embodiment, the tissue dividing unit 220 may automatically generate and store a tissue image by reading an X-ray medical image stored in a cloud system or a storage space of a computer. For example, when a new X-ray medical image is stored in a predetermined storage location (or a directory or the like), the tissue dividing unit 220 may generate a tissue image for the X-ray medical image and store the generated tissue image in the predetermined storage location. Alternatively, when the tissue dividing unit 220 receives an X-ray medical image from an external terminal connected through the Internet or the like, the tissue dividing unit 220 may transmit a tissue image generated based on the X-ray medical image to the external terminal. According to an embodiment, a separate platform for receiving an X-ray medical image from an external terminal and transmitting a tissue image may exist.

When the volume calculating unit 230 receives a two-dimensional X-ray medical image, the volume calculating unit 230 calculates the three-dimensional size, volume, or weight of at least one or more tissues by using an artificial intelligence model. For example, when the volume calculating unit 230 receives an X-ray medical image for the chest, the volume calculating unit 230 may obtain the area, volume, or weight of a lung area, an area of inflammation existing in the lung area, or the size, volume, or weight of a tumor or the like, by using an artificial intelligence model that is trained by the training unit 210 to obtain the three-dimensional size, volume, or weight of lung-related tissue. As another example, the volume calculating unit 230 may calculate the three-dimensional size, volume, or weight by inputting a tissue image (or the boundary (or area) and a brightness value of tissue) obtained by the tissue dividing unit 220.

Figure 3:
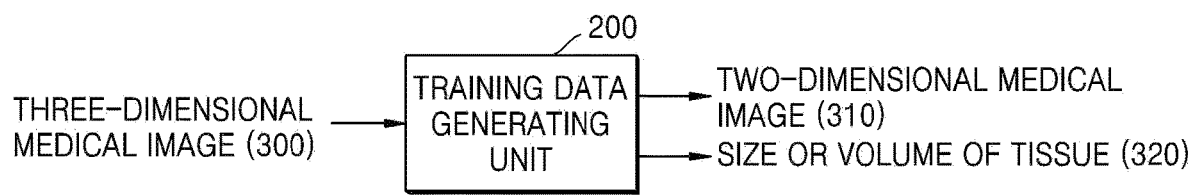
FIG. 3 is a diagram illustrating an example of a method of generating training data, according to an embodiment of the present disclosure.

FIG. 3 is a diagram illustrating an example of a method of generating training data, according to an embodiment of the present disclosure.

Referring to FIG. 3, the training data generating unit 200 automatically generates training data including a two-dimensional medical image 310 or the size, volume, or weight 320 of a tissue, or the like, by using a three-dimensional medical image 300. An example of the three-dimensional medical image 300 is shown in FIG. 3.

First, an operation of generating, from an X-ray medical image, training data necessary for training an artificial intelligence model that outputs a tissue image including at least one or more tissues or a tissue image in which at least one or more tissues have been removed is described.

The training data generating unit 200 segments normal or diseased tissue from a three-dimensional medical image. For example, in a case of training an artificial intelligence model that outputs a tissue image including only lung tissue from an X-ray medical image for the chest, the training data generating unit 200 segments lung tissue from a three-dimensional medical image for the chest. The training data generating unit 200 may segment a three-dimensional area of particular tissue from a three-dimensional medical image by using various algorithms for area segmentation in the related art. For example, the training data generating unit 200 may segment an area of particular tissue from a three-dimensional medical image by using segmentation methods described in "airway extraction method and device" of Korean Registered Patent Publication No. 10-1482247, "lung lobe extraction method and device" of Korean Registered Patent Publication No. 10-1514003, "method and device for area division of medical images" of Korean Public Patent Publication No. 10-2018-0098984, or the like.

Figure 5:
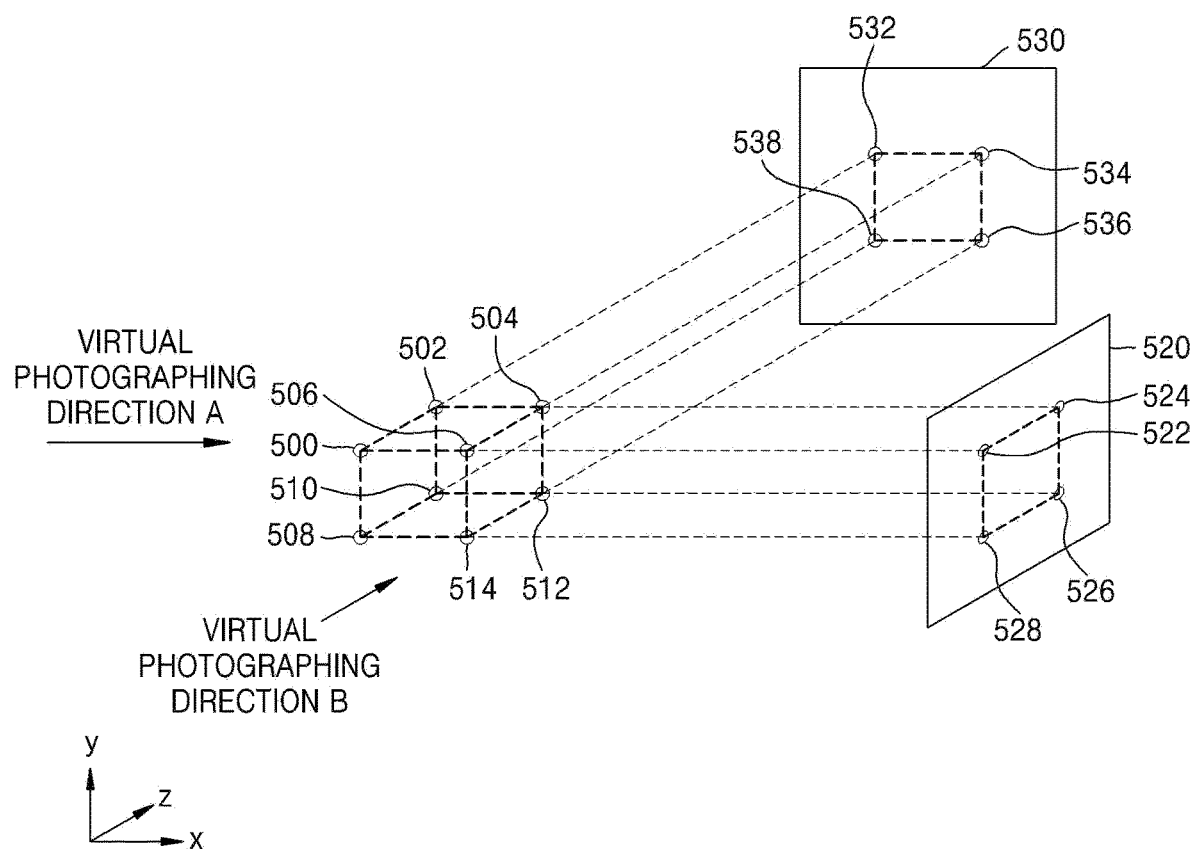
FIG. 5 is a diagram illustrating an example of a method of reducing the dimension of a three-dimensional medical image, according to an embodiment of the present disclosure.

The training data generating unit 200 generates a two-dimensional medical image (hereinafter, referred to as a basic image) such as an X-ray medical image by reducing the dimension of a three-dimensional medical image, and also generates a two-dimensional medical image (hereinafter, referred to as a segmentation image) by reducing the dimension of divided tissue from a three-dimensional medical image. For example, the training data generating unit 200 may generate a two-dimensional basic image for the chest by reducing the dimension of a three-dimensional medical image of the chest, and generate a two-dimensional segmentation image obtained by reducing the dimension of a lung area divided from the three-dimensional medical image. An example of a method of reducing the dimension of a three-dimensional medical image is shown in FIG. 5. A segmentation image may include information about a boundary (or area) and brightness value of segmented tissue. When training data including a basic image and a segmentation image is generated, the training unit 210 then trains an artificial intelligence model by using the training data.

Next, an operation of generating training data necessary for training an artificial intelligence model that calculates the three-dimensional size, volume, or weight of tissue from an X-ray medical image is described.

The training data generating unit 200 segments normal or diseased tissue from a three-dimensional medical image, and obtains the three-dimensional size, volume, or weight of the corresponding tissue. Various algorithms for obtaining the three-dimensional size, volume, or weight of tissue divided from a three-dimensional medical image in the related art may be applied to the present embodiment. The training data generating unit 200 generates a two-dimensional medical image (i.e., a basic image), such as an X-ray medical image, by reducing the dimension of a three-dimensional medical image. When training data including a two-dimensional basic image and the three-dimensional size, volume, or weight of tissue is generated, the training unit 210 then uses the training data to train an artificial intelligence model. Because the basic image includes information about boundaries (or areas) and brightness values for various tissues, the training data generating unit 200 may generate the basic image as training data, generate information about a boundary (or area) and brightness value of tissue identified in the basic image as training data, or generate the basic image and information about a boundary (or area) and brightness value of tissue in the image together as training data.

As another embodiment, training data may include a two-dimensional medical image (that is, a segmentation image) of tissue for which the three-dimensional size, volume, or weight thereof is to be obtained, rather than a basic image obtained by reducing the dimension of a three-dimensional medical image. In this case, the training unit 210 may train an artificial intelligence model by using training data including a segmentation image for tissue and the three-dimensional size, volume, or weight of the tissue. At this time, because a segmentation image includes information about a boundary (or area) and brightness value for tissue, the training data generating unit 200 may generate the segmentation image as training data, generate information about a boundary (or area) and brightness value of tissue identified in the segmentation image as training data, or generate the segmentation image and information about a boundary (or area) and brightness value of tissue together as training data. Hereinafter, a two-dimensional medical image (e.g., a basic image, a segmentation image, a tissue image, or the like) input to an artificial intelligence model may be interpreted as an image, information about a boundary (or area) and brightness value of tissue included in the image, or both of the above, according to an embodiment.

As another embodiment, training data may also include a basic image, a segmentation image, and the three-dimensional size, volume, or weight of tissue. As another embodiment, training data may include at least two or more two-dimensional medical images (basic image or segmentation image) in different directions and information about the three-dimensional size, volume, or weight of tissue, and an example thereof is shown in FIG. 6.

For convenience of description, the present embodiment describes each of an artificial intelligence model that outputs a tissue image and an operation of generating training data for an artificial intelligence model that outputs the three-dimensional size, volume, or weight of tissue. However, one artificial intelligence model may output both of a tissue image and the three-dimensional size, volume, or weight of tissue. In this case, the training data generating unit 200 may generate training data including a basic image, a segmentation image, and the three-dimensional size, volume, or weight of tissue at one time. As another embodiment, the tissue analysis device 100 may include each of a first artificial intelligence model that outputs a tissue image and a second artificial intelligence model that outputs the three-dimensional size, volume, or weight of tissue, and an example thereof is shown in FIG. 7.

Figure 4:
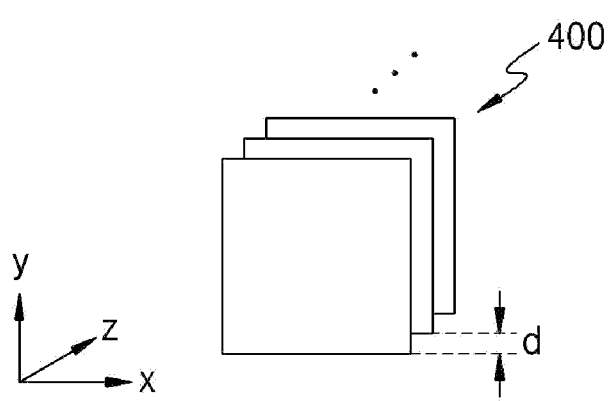
FIG. 4 is a diagram illustrating an example of a three-dimensional medical image according to an embodiment of the present disclosure.

FIG. 4 is a diagram illustrating an example of a three-dimensional medical image according to an embodiment of the present disclosure.

Referring to FIG. 4, a three-dimensional medical image 400, such as computed tomography (CT) or the like, may include a plurality of x-y cross-sectional images captured at a certain distance d. The three-dimensional medical image 400 may include three-dimensional voxels indicating brightness, and may be stored as a digital imaging and communication in medicine (DICOM) file.

FIG. 5 is a diagram illustrating an example of a method of reducing the dimension of a three-dimensional medical image, according to an embodiment of the present disclosure.

Referring to FIG. 5, a three-dimensional image including voxels 500, 502, 504, 506, 508, 510, 512, and 514 including brightness values. For convenience of description, the present embodiment shows only eight voxels 500, 502, 504, 506, 508, 510, 512, and 514 for a three-dimensional medical image.

The training data generating unit 200 projects a three-dimensional medical image onto virtual planes 520 and 530 in a certain direction to reduce the dimension of the three-dimensional medical image to a two-dimensional medical image. Images projected on the virtual planes 520 and 530 become two-dimensional medical images. At this time, the training data generating unit 200 generates a brightness value of the two-dimensional medical image by averaging brightness values of voxels overlapping in a projection direction. That is, because a brightness value of an X-ray medical image is influenced by at least one or more tissues positioned in an X-ray transmission direction, in the present embodiment, to generate a two-dimensional medical image in which an effect of each of tissues is reflected, such as an X-ray medical image, from a three-dimensional medical image, a brightness value of each pixel of the two-dimensional medical image is obtained by averaging brightness values of voxels overlapping in a projection direction.

For example, when a virtual photographing direction (that is, a projection direction) is parallel to an X-axis, the training data generating unit 200 generates a brightness value of a first pixel 522 of a two-dimensional medical image projected on the virtual plane 520 by averaging brightness values of a first voxel 500 and a second voxel 506, which overlap in the projection direction. In this way, the training data generating unit 200 may generate a brightness value of a second pixel 524 by averaging brightness values of third and fourth voxels 502 and 504, generate a brightness value of a third pixel 528 by averaging brightness values of fifth and sixth voxels 508 and 514, and generate a brightness value of a fourth pixel 526 by averaging brightness values of seventh and eighth voxels 510 and 512.

According to an embodiment, the training data generating unit 200 may generate two-dimensional images in various projection directions for one three-dimensional image. For example, when a virtual photographing direction is parallel to a Z-axis, the training data generating unit 200 may generate a two-dimensional medical image by obtaining a brightness value of each of pixels 532, 534, 536, and 538, which are projected on the virtual plane 530, by averaging brightness values of each of voxels 500, 502, 504, 506, 508, 510, 512, and 514, which overlap in a Z-axis direction.

FIG. 6 is a diagram illustrating an example of an artificial intelligence model that obtains the size, volume, or weight of tissue from an X-ray medical image, according to an embodiment of the present disclosure.

Referring to FIG. 6, the training unit 210 of the tissue analysis device 100 may train an artificial intelligence model 600 by using training data including at least two or more medical images in different directions for normal or diseased tissue and the three-dimensional size, volume, or weight of the tissue. For example, in an embodiment of FIG. 5, two-dimensional images in different directions in the training data may be a two-dimensional medical image (or information about a boundary (or area) and brightness value of an area generated by projecting a three-dimensional medical image in an X-axis direction) in which the three-dimensional medical image is projected in the X-axis direction and a two-dimensional medical image (or information about a boundary (or area) and brightness value of an area generated by projecting a three-dimensional medical image in a Z-axis direction) in which a three-dimensional medical image is projected in the Z-axis direction. Here, the two-dimensional medical image may be a basic image or a segmentation image described with reference to FIG. 3.

When the artificial intelligence model 600 receives training data including two or more medical images in different directions (or information about a boundary (or area) and brightness value), the artificial intelligence model 600 predicts and outputs the three-dimensional size, volume, or weight of tissue. The artificial intelligence model 600 performs a training operation of adjusting a connection weight of the artificial intelligence model 600 by comparing the predicted size, volume, or weight with the size, volume, or weight of tissue included in the training data.

When training for the artificial intelligence model 600 is completed, the volume calculating unit 230 of the tissue analysis device 100 may identify the three-dimensional size, volume, or weight for particular tissue by inputting at least two or more X-ray medical images captured in different directions to the artificial intelligence model. For example, when the volume calculating unit 230 receives an X-ray medical image for the chest in a front direction and an X-ray medical image for the chest in a lateral direction, the volume calculating unit 230 may input the X-ray medical images to the artificial intelligence model 600, which has been trained to identify the size, volume, or weight of a lung area (or lesion or inflammation, or the like). Because volume is a physical quantity that represents the size of a space, it may be more accurate to obtain a volume of tissue from an X-ray medical image captured in at least two or more directions than to obtain a volume of tissue from an X-ray medical image captured in any one direction.

As another embodiment, when the tissue analysis device 100 receives at least two or more X-ray medical images in different directions, the tissue analysis device 100 may output a three-dimensional tissue image based on the received at least two or more X-ray medical images. To this end, the tissue analysis device 100 may generate training data including at least two or more two-dimensional medical images in different directions and a three-dimensional image of tissue by using a three-dimensional medical image and train the artificial intelligence model 600 by using the training data. For example, when the tissue analysis device 100 receives an X-ray medical image for a front surface and a side surface of the chest, the tissue analysis device 100 may generate a three-dimensional medical image for a lung area by using the artificial intelligence model 600, which has been trained.

FIG. 7 is a diagram illustrating another example of an artificial intelligence model according to an embodiment of the present disclosure.

Referring to FIG. 7, the tissue analysis device 100 includes a first artificial intelligence model 700 that outputs a tissue image and a second artificial intelligence model 710 that outputs the volume, size, or weight of tissue.

The first artificial intelligence model 700 is an artificial intelligence model trained to output images (that is, tissue images) for at least one or more tissues by using a basic image and a segmentation image described with reference to FIG. 3. That is, when the first artificial intelligence model 700, which has been trained, receives a two-dimensional X-ray medical image, the first artificial intelligence model 700 may segment particular tissue from the X-ray medical image to output a tissue image (and/or information about a boundary (or area) and brightness value) including only the particular tissue or a tissue image (and/or information about a boundary (or area) and brightness value) excluding only the particular tissue from the X-ray medical image.

The second artificial intelligence model 710 is an artificial intelligence model trained by using training data including a two-dimensional medical image and the three-dimensional size, volume, or weight of tissue. A two-dimensional medical image may be a tissue image (and/or information about a boundary (or area) and brightness value) output from the first artificial intelligence model 700. For example, when the first artificial intelligence model 700 receives an X-ray medical image to output a tissue image, the second artificial intelligence model 710, which has been trained, may identify and output the three-dimensional size, volume, or weight of tissue from the tissue image received from the first artificial intelligence model 700.

Figure 8:
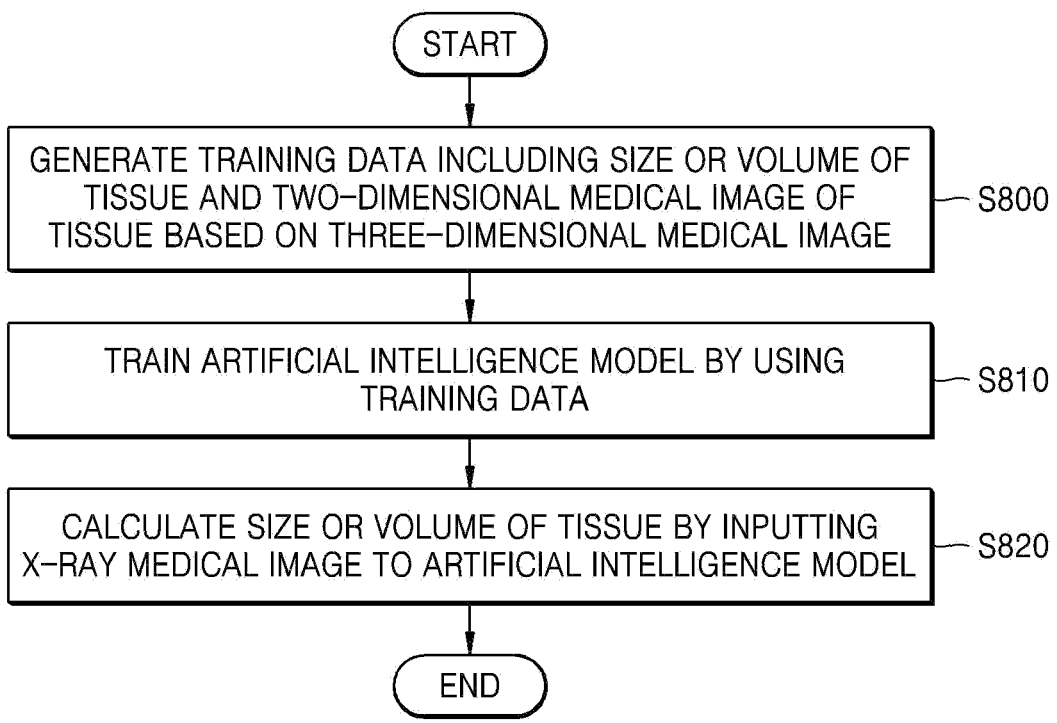
FIG. 8 is a flowchart illustrating an example of a method of obtaining the size, volume, or weight of human tissue, according to an embodiment of the present disclosure.

FIG. 8 is a flowchart illustrating an example of a method of obtaining the size, volume, or weight of human tissue, according to an embodiment of the present disclosure.

Referring to FIG. 8, in operation S800, the tissue analysis device 100 generates training data including a two-dimensional medical image and information about the size, volume, or weight of tissue by using a three-dimensional medical image. The training data may include a two-dimensional medical image in any one direction or at least two or more two-dimensional medical images in different directions as shown in FIG. 6. As another example, a two-dimensional medical image included in training data may be a basic image or a segmentation image described with reference to FIG. 3.

In operation S810, the tissue analysis device 100 trains, by using the training data, an artificial intelligence model that obtains the size, volume, or weight by dividing at least one or more tissues from a two-dimensional medical image in which a plurality of tissues are displayed overlapping on the same plane. As another example, when the training data includes at least two or more two-dimensional medical images in different directions, an artificial intelligence model may be trained by using the two-dimensional medical images in different directions and information about the size, volume, or weight of tissue. As another example, the tissue analysis device 100 may train a model in which a first artificial intelligence model that segments at least one or more tissues from a two-dimensional medical image in which a plurality of tissues are displayed overlapping on the same plane and a second artificial intelligence model that obtains the three-dimensional size, volume, or weight of divided tissue are sequentially connected, as shown in FIG. 7.

In operation S820, the tissue analysis device 100 obtains the three-dimensional size, volume, or weight of tissue by inputting an X-ray medical image to the artificial intelligence model, which has been trained. When the artificial intelligence model is a model trained based on at least two or more two-dimensional medical images in different directions, the tissue analysis device 100 may obtain the three-dimensional size, volume, or weight of tissue by inputting at least two or more X-ray medical images in different directions to the artificial intelligence model. As another embodiment, the tissue analysis device 100 may generate a three-dimensional image by inputting at least two or more two-dimensional X-ray medical images in different directions to the artificial intelligence model. As another embodiment, the tissue analysis device 100 may generate a plurality of two-dimensional or three-dimensional tissue images obtained by segmenting a plurality of tissues included in a two-dimensional X-ray medical image by using an artificial intelligence model.

The present disclosure may also be implemented as computer-readable code on a computer-readable recording medium. The computer-readable recording medium includes all types of recording devices in which data readable by a computer system is stored. Examples of the computer-readable recording medium include read-only memory (ROM), random-access memory (RAM), a compact disc read-only memory (CD-ROM), magnetic tape, a floppy disk, and an optical data storage device. In addition, the computer-readable recording medium may be distributed in a network-connected computer system, so that computer-readable code may be stored and executed in a distributed manner.

With respect to the present disclosure, preferred embodiments have been described. Those of ordinary skill in the art to which the present disclosure pertains will understand that the present disclosure may be implemented in a modified form without departing from the essential characteristics of the present disclosure. Therefore, disclosed embodiments are to be considered in an illustrative rather than a restrictive sense. The scope of the present disclosure is indicated in the claims rather than the above description, and all differences within the scope equivalent thereto should be construed as being included in the present disclosure.

The invention claimed is:

1. A tissue analysis method comprising:
   generating training data including a two-dimensional medical image and information about a three-dimensional size, volume, or weight of tissue by using a three-dimensional medical image;
   training, by using the training data, an artificial intelligence model that obtains a three-dimensional size, volume, or weight of tissue by segmenting at least one or more normal or diseased tissues from a two-dimensional medical image in which a plurality of tissues are displayed overlapping on a same plane; and
   obtaining a three-dimensional size, volume, or weight of normal or diseased tissue by inputting an X-ray medical image to the artificial intelligence model,
   wherein the generating of the training data comprises:
   generating training data comprising two or more two-dimensional medical images for the tissue by projecting the three-dimensional medical image in different projection directions,
   wherein the training of the artificial intelligence model comprises:

inputting two or more two-dimensional medical images of the training data to the artificial intelligence model; and performing a training operation of the artificial intelligence model by comparing a predicted three-dimensional size, volume or weight predicted by the artificial intelligence with a three-dimensional size, volume or weight included in the training data, wherein the obtaining the three-dimensional size, volume, or weight comprises:

receiving two or more X-ray medical images captured in different direction;

inputting the two or more X-ray medical images to the trained artificial intelligence model; and obtaining the three-dimensional size, volume, or weight for the normal or diseased tissue of the X-ray medical images.

2. The tissue analysis method of claim 1, wherein the training of the artificial intelligence model comprises:

training a first artificial intelligence model to segment at least one or more tissues from a two-dimensional medical image in which a plurality of tissues are displayed overlapping on the same plane; and training a second artificial intelligence model that obtains a three-dimensional size, volume, or weight of tissue divided through the first artificial intelligence model.

3. The tissue analysis method of claim 1, further comprising generating a plurality of tissue images obtained by segmenting a plurality of tissues included in the X-ray image by using the artificial intelligence model.

4. A computer-readable recording medium in which a program for performing the method according to claim 1 is recorded.

5. A tissue analysis device which is implemented as a computer, comprising:

a training data generating unit configured to generate training data including a two-dimensional medical image and information about a three-dimensional size, volume, or weight of tissue by using a three-dimensional medical image;

a training unit configured to, by using the training data, train an artificial intelligence model that obtains a three-dimensional size, volume, or weight of tissue by dividing at least one or more normal or diseased tissues from a two-dimensional medical image in which a plurality of tissues are displayed overlapping on a same plane; and a volume calculating unit configured to obtain a three-dimensional size, volume, or weight of normal or diseased tissue by inputting an X-ray medical image to the artificial intelligence model, wherein the training data generating unit configured to generate training data comprising two or more two-dimensional medical images for the tissue by projecting the three-dimensional medical image in different projection directions, wherein the training unit configured to input two or more two-dimensional medical images of the training data to the artificial intelligence model, and to perform a training operation of the artificial intelligence model by comparing a predicted three-dimensional size, volume or weight predicted by the artificial intelligence with a three-dimensional size, volume or weight included in the training data, wherein the volume calculation unit configured to receive two or more X-ray medical images captured in different direction, and input the two or more X-ray medical images to the trained artificial intelligence model, and obtain the three-dimensional size, volume, or weight for the normal or diseased tissue of the X-ray medical images.

6. The tissue analysis device of claim 5, further comprising a tissue dividing unit configured to generate a plurality of tissue images obtained by segmenting a plurality of tissues included in the X-ray image by using the artificial intelligence model.

* * * * *